United States Patent
Ohkubo (10) Patent No.: US 7,576,866 B2
(45) Date of Patent: Aug. 18, 2009

(54) OPTICAL TOMOGRAPHY SYSTEM

(75) Inventor: Kazunobu Ohkubo, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 349 days.

(21) Appl. No.: 11/714,854

(22) Filed: Mar. 7, 2007

(65) Prior Publication Data

US 2007/0211255 A1    Sep. 13, 2007

(30) Foreign Application Priority Data

Mar. 7, 2006  (JP) .............................. 2006-060505

(51) Int. Cl.
G01B 9/02    (2006.01)
(52) U.S. Cl. ...................... 356/479; 356/495
(58) Field of Classification Search ................ 356/456, 356/477, 479, 491, 495, 497; 250/227.19, 250/227.27; 385/12
See application file for complete search history.

(56) References Cited

U.S. PATENT DOCUMENTS 7,042,573 B2 * 5/2006 Froggatt ..................... 356/479

2006/0055936 A1 * 3/2006 Yun et al. ..................... 356/479
2007/0035743 A1 * 2/2007 Vakoc et al. ................ 356/495

FOREIGN PATENT DOCUMENTS

JP    2000-46729 A    2/2000

OTHER PUBLICATIONS

Mitsuo Takeda, "Optical Frequency Scanning Interference Microscopes", Optical Engineering Contact, vol. 41, No. 7, 2003, pp. 426-432, Partial English Translation.

* cited by examiner

Primary Examiner—Michael A Lyons
(74) Attorney, Agent, or Firm—Sughrue Mion, PLLC (57) ABSTRACT

In an optical tomography system, an interference light obtained by multiplexing the reflected light from the object and the reference light is guided to an interference light detecting means by a waveguide means. The interference light detecting means has a spectrometer spectrally dividing the interference light. A polarization setting means which causes the interference light guided by the waveguide means to enter the spectrometer after setting the state of polarization of the interference light guided by the waveguide means to a predetermined state of polarization is provided between the waveguide means and the spectrometer.

5 Claims, 4 Drawing Sheets

FIG.9

OPTICAL TOMOGRAPHY SYSTEM

BACKGROUND OF THE INVENTION

1. Field of the Invention

This invention relates to an optical tomography system for obtaining an optical tomographic image by measurement of OCT (optical coherence tomography).

2. Description of the Related Art

When obtaining tomographic image of an object of measurement in a body cavity, there has been sometimes used an optical tomography system employing the measurement of OCT. In the optical tomography system, low coherence light emitted from a light source is divided into measuring light and reference light and the measuring light is projected onto the object of measurement, while the reflected light from the object of measurement is multiplexed with the reference light, and a tomographic image is obtained on the basis of the intensity of the interference light of the reflected light and the reference light.

In the optical tomography system, there has been known a system using the TD-OCT (time domain OCT) measurement where the measuring position in the direction of the object is changed by changing the optical path length of the reference light.

Further, recently, as a system of rapidly obtaining a tomographic image without changing the optical path length of the reference light, there has been proposed an SD-OCT system using an SD-OCT (spectral domain OCT) measurement. In the SD-OCT measurement, a tomographic image is formed without scanning in the direction of depth, by dividing broadband, low coherence light from a light source by the use of a Michelson interferometer, and carrying out a Fourier analysis on each channeled spectrum obtained by decomposing the interference light of the reflected light, which returns when projecting the measuring light onto the object, and the reference light into frequency components.

In the SD-OCT system, frequency analysis is carried out on the interference light by the use of a spectrometer which spectrally divides the interference light and a detector which detects by the frequencies the intensities of the light spectrally divided by the spectrometer. In Japanese Unexamined Patent Publication No. 2000-046729, there is disclosed an SD-OCT system in which a diffractive optics is employed as the spectrometer.

Figure 9:
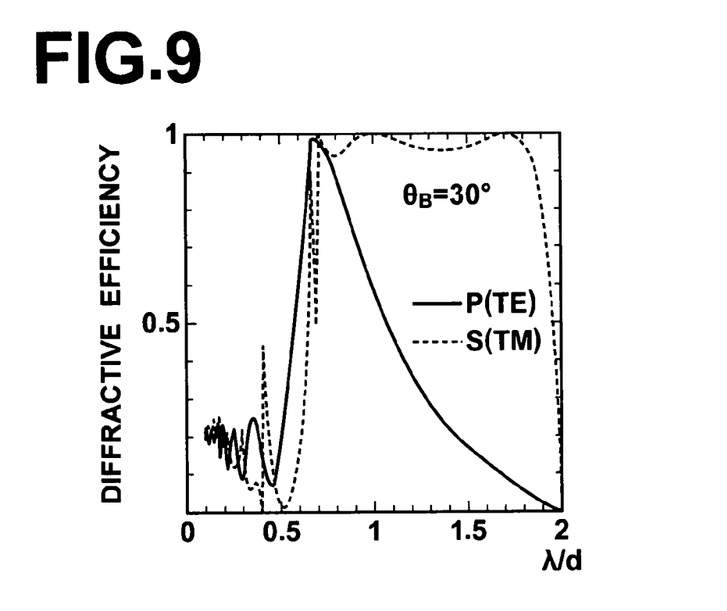
FIG. 9 is a view showing polarization characteristics of the diffractive optics.

However, since the diffractive optics exhibits polarization characteristics, the output of the spectrometer differs depending on the state of polarization of light impinging upon the spectrometer. For example, as shown in FIG. 9, light where the direction of vibration of the electric field vector is parallel to the groove of the diffractive optics (S-polarization: shown in broken line) differs in diffracting efficiency from light where the direction of vibration of the electric field vector is perpendicular to the groove of the diffractive optics (P-polarization: shown in solid line). In FIG. 9, the abscissa represents $\lambda/d$ which is the ratio of the pitches d of the lattices in the diffractive optics and the wavelength of the incident light and the ordinate represents the diffracting efficiency when the blaze angle $\theta B$ is $30°$. As shown in FIG. 9, when $\lambda/d=1$, the diffracting efficiency is almost 1 in the case of the S-polarization, whereas the same is only about 0.6 in the case of the P-polarization. That is, in the case where the interference light is linearly polarized, there generates a difference close to about twice in the diffracting efficiency depending upon the direction of the polarization of the interference light. Since the difference in the diffracting efficiency appears as a difference in the intensity, the wavelength spectrum output from the spectrometer fluctuates according to the state of polarization.

In an optical tomography system applied to an endoscope, a fiber is employed to guide light to a body cavity. The fiber is inherently folded or twisted since it is inserted into a body cavity. Further, a temperature change of the fiber inherent to insertion of a body cavity is necessarily generated. In a single-mode fiber which is generally used for an endoscope, polarization of light propagating through the fiber changes due to the stress by folding or twisting or a temperature change. Further, in an endoscope, light is often caused to be polarized and to make one rotation in a circumferential direction of the fiber. When the light makes one rotation, the direction of polarization is rotated by $360°$. Due to these facts, the state of polarization of the interference light guided through the fiber during measurement is not constant but fluctuates.

When the fluctuating interference light impinges upon the spectrometer, the wavelength spectrum changes and the change is considered to be error in the case of the spectrometers exhibiting polarization characteristics. The level of a signal obtained by Fourier-transform of the wavelength spectrum also fluctuates and as a result, a tomographic image deteriorates in image quality.

Further, in the SD-OCT system, a broad-band light source is necessary to ensure a high resolution, which involves the following problem due to the polarization characteristics. For example, when a light source which is 1 μm in central wavelength, and 200 nm in wavelength width is used, and a diffractive optics which is 1 μm in pitches d of the lattices is used as the spectrometer, $\lambda/d$ is 0.9 to 1.1 since the wavelength band of the light source is 900 to 1100 nm. In this case, in accordance with FIG. 9, the diffracting efficiency is almost unchanged in the case of the S-polarization, whereas the same is 0.5 to 0.7 according to the wavelength in the case of the P-polarization.

SUMMARY OF THE INVENTION

In view of the foregoing observations and description, the primary object of the present invention is to provide an optical tomography system in which deterioration in image quality due to change in polarization of the interference light can be prevented.

In accordance with the present invention, there is provided an optical tomography system comprising a light source which emits light, a light dividing means which divides the light emitted from the light source into measuring light and reference light, a multiplexing means which multiplexes the reflected light from the object when the measuring light emitted is projected onto the object and the reference light, an interference light detecting means which has a spectrometer spectrally dividing interference light of the reflected light which has been multiplexed by the multiplexing means and detects the reference light which has been spectrally divided by the spectrometer, a waveguide means which guides the interference light to the interference light detecting means and a tomographic image obtaining means which obtains a tomographic image of the object on the basis of the interference light detected by the interference light detecting means, wherein the improvement comprises that a polarization setting means which causes the interference light guided by the waveguide means to enter the spectrometer after setting the state of polarization of the interference light guided by the waveguide means to a predetermined state of polarization is provided between the waveguide means and the spectrometer.

"State of polarization" means, for instance, P-polarized light, S-polarized light, linearly polarized light other than P-polarized light and S-polarized light, right elliptically polarized light, left elliptically polarized light, right circularly polarized light or left circularly polarized light. Further, "State of polarization" as used here includes non-polarized light where lineally polarized light polarized in each of these directions, elliptically polarized light polarized in each of these elliptical directions and circularly polarized light polarized in each of these circular directions are all superimposed one on another.

"Waveguide means" as used here means a medium for propagating light such as an optical fiber or a light guide and includes a bulk optical system arranged to guide the interference light from the multiplexing means to the interference light detecting means.

The state of polarization set by the polarization setting means may be linearly polarized light or non-polarized light. In the former case, the polarization setting means may once divide the interference light into two bundles of linearly polarized light which are perpendicular to each other in the direction of polarization and then synthesize them after changing the direction of polarization of one of them to be the same as the other. In this case, it is preferred that an optical path length adjusting means which adjusts the optical path length of one of the two bundles of linearly polarized light be provided.

In accordance with the present invention, since even if the state of polarization of the interference light which impinges upon the interference light detecting means by way of the waveguide means changes, the polarization setting means sets the state of polarization to a predetermined state of polarization before it impinges upon the spectrometer, light impinges upon the spectrometer constantly in the same state of polarization. Accordingly, even if the spectrometer has polarization characteristics, the wavelength spectrum output from the spectrometer cannot be changed with change of the state of polarization of the interference light, and deterioration of the tomographic image can be prevented.

When the polarization setting means once divides the interference light into two bundles of linearly polarized light which are perpendicular to each other in the direction of polarization and then synthesizes them after changing the direction of polarization of one of them to be the same as the other, deterioration of the tomographic image can be prevented by setting the state of polarization of interference light to linearly polarized light in the direction where the influence of polarization is the least taking into account the characteristics of the spectrometer to the linearly polarized light in each direction, for instance, shown in FIG. 9.

When an optical path length adjusting means which adjusts the optical path length of one of the two bundles of linearly polarized light is provided, interference of the two bundles of the linearly polarized light to be synthesized can be prevented.

When the polarization setting means sets the state of polarization of interference light to non-polarized light, since the interference light becomes light where the polarized lights of various kinds polarized in various directions mingle each other and there is no polarization-dependency, even if a factor which fluctuates the state of polarization arises, deterioration of the tomographic image can be prevented without affected thereby.

DESCRIPTION OF THE PREFERRED EMBODIMENTS

Figure 1:
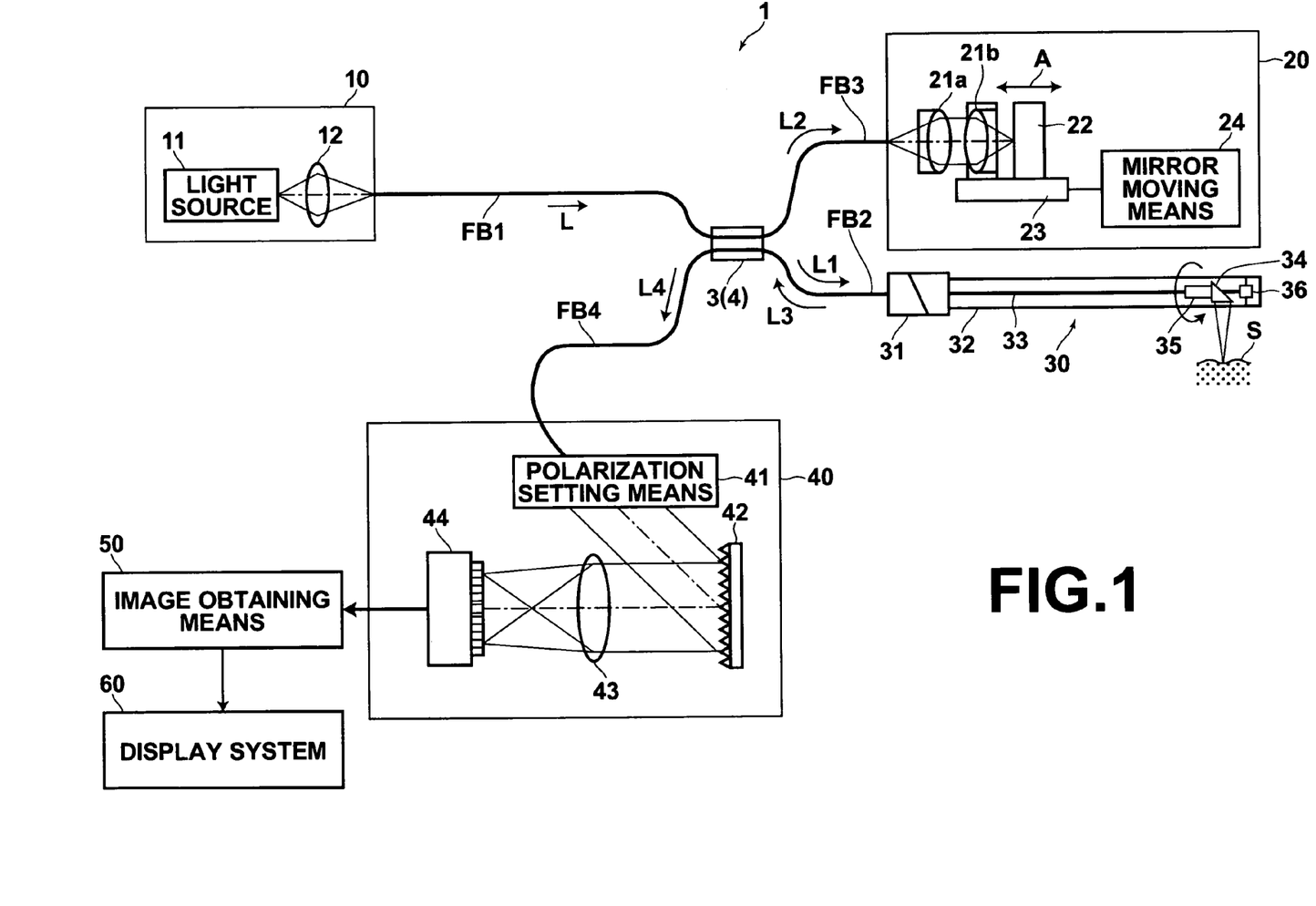
FIG. 1 is a view showing an optical tomography system in accordance with a first embodiment of the present invention.

Embodiments of the optical tomography system of the present invention will be described in detail with reference to the drawings, hereinbelow. FIG. 1 is a view that illustrates an optical tomography system in accordance with a first embodiment of the present invention. The optical tomography system 1 of this embodiment is for obtaining a tomographic image of an object of measurement such as a living tissue or a cell in a body cavity by measuring the SD-OCT. The optical tomography system 1 of this embodiment comprises: a light source unit 10 which emits light L; a light dividing means 3 which divides the light L emitted from the light source unit 10 into measuring light beam L1 and reference light beam L2; an optical path length adjusting means 20 which adjusts the optical path length of the reference light beam L2 divided by the light dividing means; a probe 30 which guides to the object S to be measured the measuring light beam L1 divided by the light dividing means 3; a multiplexing means 4 for multiplexing a reflected light beam L3 from the object S when the measuring light beam L1 is irradiated onto the object S from the probe 30, and the reference light beam L2; an interference light detecting means 40 for detecting interference light beam L4 of the reflected light beam L3 and the reference light beam L2 which have been multiplexed by the multiplexing means 4; and an image obtaining means 50 which detects intensities the measuring light L1 in positions in the direction of depth of the object by carrying out frequency-analysis on the interference light L4 detected by the interference light detecting means 40 and obtains a tomographic image of the object S.

The light source unit 10 comprises a light source 11 which emits low coherence light L such as an SLD (super luminescent diode), ASE (amplified spontaneous emission) and an optical system 12 which enters the light emitted from the light source 11 into an optical fiber FB1. Since the optical tomography system 1 of this embodiment is for obtaining a tomographic image with a living tissue in a body cavity taken as the object S, it is preferred that the light source 11 be, for instance, a broad spectral band, ultra short pulse laser where attenuation of light due to scatter and/or absorption when transmitted through the object S is minimized.

The light dividing means 3 of FIG. 1 comprises, for instance, a 2×2 fiber optic coupler and divides the laser beam L led thereto by way of the optical fiber FB1 from the light source unit 10 into the measuring light beam L1 and the reference light beam L2. The light dividing means 3 is optically connected to two optical fibers FB2 and FB3, and the measuring light beam L1 is propagated through the optical fiber FB2 while the reference light beam L2 is propagated through the optical fiber FB3. In this embodiment, the light dividing means 3 also functions as the multiplexing means 4.

The probe 30 is optically connected to the optical fiber FB2 and the measuring light beam L1 is guided to the probe 30 from the optical fiber FB2. The probe 30 is inserted into a body cavity, for instance, through a forceps port by way of a forceps channel and is removably mounted on the optical fiber FB2 by an optical connector OC.

The optical probe 30 comprises: a cylindrical probe outer envelope 32 having a closed front end; a single optical fiber 33, which is provided inside the outer envelope 32 to extend in the direction of the axis of the outer envelope 32; a prism mirror 34 rotating light L1 emitted from the front end of the optical fiber 13 in the circumferential direction of the probe outer envelope 32, and a rod lens 35 which collects light L1 emitted from the front end of the optical fiber 33 to converge on the object S to be scanned which is disposed externally of the circumference of the outer envelope 32 and a motor 36 which rotates the prism mirror 34 about the axis of the optical fiber 33.

An optical path length adjusting means 20 is disposed on the side of the optical fiber FB3 radiating the reference light beam L2. The optical path length adjusting means 20 changes the optical path length of the reference light beam L2 in order to adjust the position from which the tomographic image of the object S is initiated to be obtained and comprises a reflecting mirror 22 which reflects the reference light beam L2 radiated from the optical fiber FB3, a first lens 21a disposed between the reflecting mirror 22 and the optical fiber FB3, and a second lens 21b disposed between the first lens 21a and the reflecting mirror 22.

The first lens 21a makes parallel the reference light beam L2 radiated from the core of the optical fiber FB3 and at the same time, collects the reference light beam L2 reflected by the reflecting mirror 2 on the core of the optical fiber FB3. The second lens 21b collects the reference light beam L2 made parallel by the first lens 21a on the reflecting mirror 22 and at the same time, makes parallel the reference light beam L2 reflected by the reflecting mirror 22.

Accordingly, the reference light beam L2 radiated from the optical fiber FB3 is turned to a parallel light by the first lens 21a and is collected on the reflecting mirror 22 by the second lens 21b. Subsequently, the reference light beam L2 reflected by the reflecting mirror 22 is turned to a parallel light by the second lens 21b and is collected on the core of the optical fiber FB3 by the first lens 21a.

The optical path length adjusting means 20 is further provided with a movable stage 23 to which the second lens 21b and the reflecting mirror 22 are fixed and a mirror movement means 24 which moves the movable stage 23 in the direction of the optical axis of the first lens 21a. In response to movement of the movable stage 23 in the direction of arrow A, the optical path length of the reference light beam L2 can be changed.

The multiplexing means 4 comprises a 2×2 fiber optic coupler as described above, and multiplexes the reference light beam L2 which has been changed in its optical path length by the optical path length adjusting means 20 and the reflected light beam L3 from the object S to emit the interference light beam L4 toward the interference light detecting means 40 by way of an optical fiber FB4 which is the waveguide means.

The interference light detecting means 40 detects the interference light L4 of the reflected light beam L3 and the reference light beam L2 which have been multiplexed by the multiplexing means, and is provided with a polarization setting means 41 for setting the state of polarization of the interference light L4 radiated from the optical fiber FB4 to a predetermined state of polarization, a spectral means 42 which spectrally divides by the wavelength band the interference light L4 with a plurality of wavelength bands which is entered from the polarization setting means 41, an optical system 43 which collects the interference lights L4 of each wavelength band spectrally divided by the spectral means 42 on a light detecting means 44, and the light detecting means 44 which detects each of the plurality of wavelength bands of the interference light L4 collected by the optical system 43.

Figure 2:
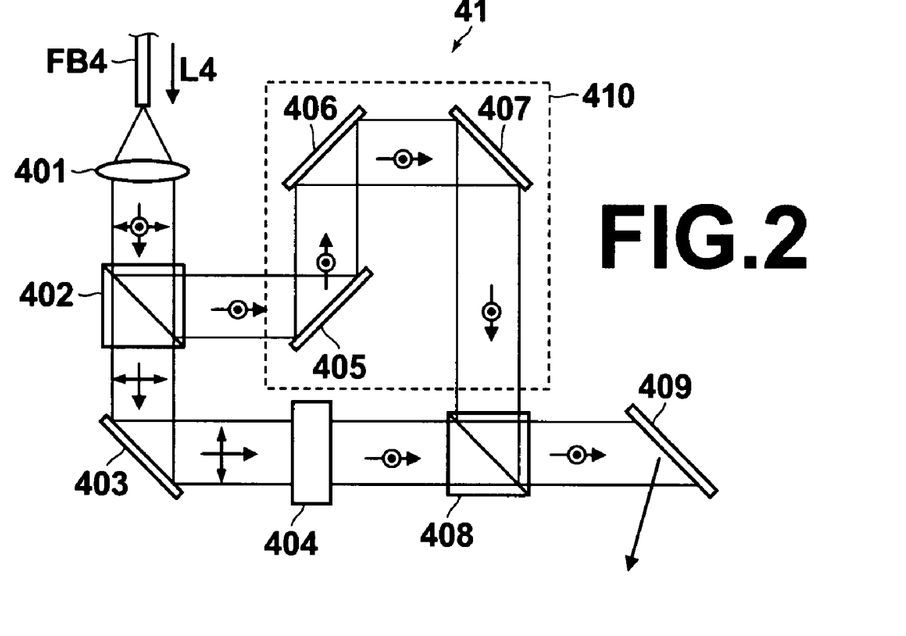
FIG. 2 is a view showing the polarization setting means of the optical tomography system of FIG. 1.

In this particular embodiment, the polarization setting means 41 sets the state of polarization of the interference light L4 to a linearly polarized light and enters the linearly polarized interference light L4 into the interference light detecting means 40. The detailed structure of the polarization setting means 41 is shown in FIG. 2. In FIG. 2, the polarization setting means 41 comprises a collimator lens 401 which makes parallel the interference light L4 from the optical fiber FB4, a polarization beam splitter 402, a mirror 403 for folding the optical path which is disposed on one of the optical paths branched by the polarization beam splitter 402, a rotating polarization element 404, mirrors 405, 406 and 407 for folding the optical path which are disposed on the other of the optical paths branched by the polarization beam splitter 402, a half-silvered prism 408 which synthesizes two branched bundles of lights, a mirror 409 which folds the optical path to enter the synthesized light into the spectral means 42 and an optical path length adjusting means 410 which adjusts the optical path length.

The polarization beam splitter 402 comprises a reflection surface which is inclined by 45° to the incident surface inside thereof and is structured like a cube sandwiching the reflection surface between the inclined surfaces of two triangle prisms, whereby the incident light is separated into P-polarized light and S-polarized light which are two linearly polarized lights. Though being a cube-type beam splitter in FIG. 2, the polarization beam splitter 402 may be of a plate-type. The rotating polarization element 404 rotates the direction of polarization by 90° and may be, for instance, a ½λ plate.

The half-silvered prism 408 comprises a reflection surface which is inclined by 45° to the incident surface inside thereof and is structured like a cube sandwiching the reflection surface between the inclined surfaces of two triangle prisms, thereby transmitting the incident light by 50% and reflecting the same by 50%. The half-silvered prism 408 functions as a multiplexing means and may be a half-silvered mirror instead of the half-silvered prism 408.

The optical path length adjusting means 410 makes one of the optical paths branched by the polarization beam splitter 402 longer than the other in coherence length by disposing the mirrors 405, 406 and 407 as shown in FIG. 2. With this arrangement, the pair of linearly polarized lights to be synthesized with their direction of polarization equalized to each other can be prevented from interfering with each other.

Figure 3:
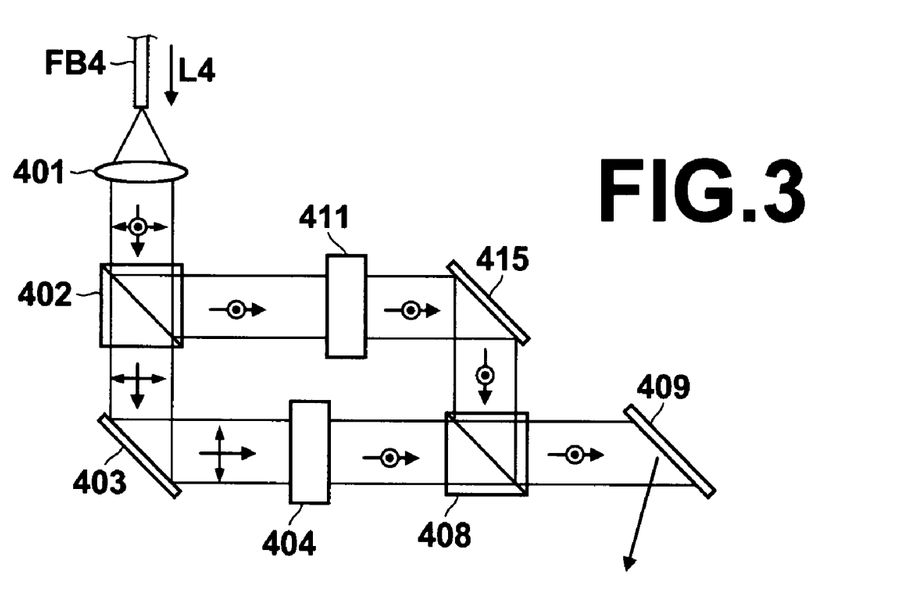
FIG. 3 is a view showing another example of the polarization setting means.

Though, in the example shown in FIG. 2, the optical path length is adjusted by forming a bypass, the optical path length adjusting means need not be limited to of such a structure but may be of a structure shown in FIG. 3 where a medium 411 of glass higher than air in refractive index is inserted into one of the two optical paths. In the structure shown in FIG. 3, light reflected by the polarization beam splitter 402 passes through the medium 411 which is higher than air in refractive index, is reflected by the folding mirror 415 and then impinges upon the half-silvered prism 408.

Figure 4:
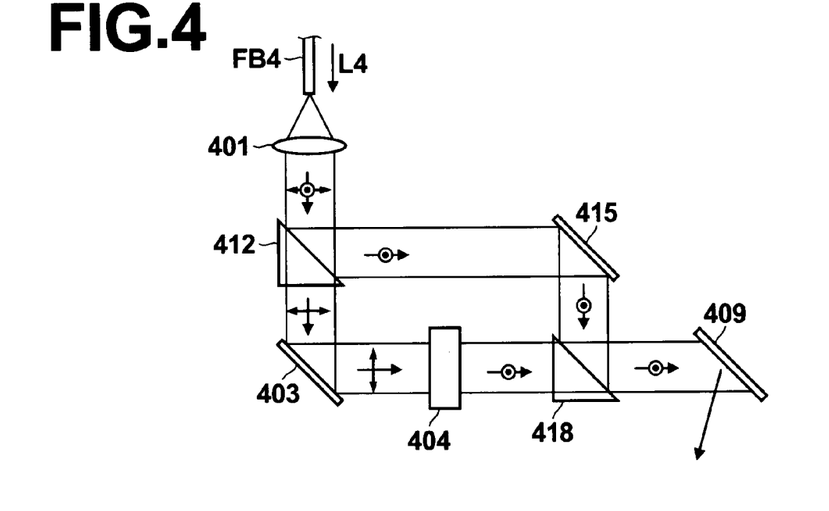
FIG. 4 is a view showing still another example of the polarization setting means.

Another example of the optical path length adjusting means will be described with reference to FIG. 4, hereinbelow. In FIG. 4, the cube type beam splitter 402 and the half-silvered prism 408 in FIG. 2 are respectively replaced by a polarization beam splitter 412 and a half-silvered prism 418 each comprising a reflection surface formed on a single triangular prism. In the structure shown in FIG. 4, light reflected by the polarization beam splitter 412 travels without passing through the prism medium, is reflected by the folding mirror 415 and then impinges upon the half-silvered prism 418 without passing through the prism medium.

As still another example of the optical path length adjusting means, at least one of the cube type beam splitter 402 and the half-silvered prism 408 in FIG. 2 may be replaced with a prism trapezoidal in cross-section where one of the triangular prisms forming the cube type beam splitter 402 and the half-silvered prism 408 is extended in the direction of the optical path.

The interference light L4 radiated from the optical fiber FB4 in the polarization setting means 41 shown in FIG. 2 is separated into P-polarized light and S-polarized light by the polarization beam splitter 402 after turned to parallel light by the collimator lens 401. The P-polarized light passing through the polarization beam splitter 402 is reflected by the mirror 403, is rotated by 90° in its direction of polarization by the rotating polarization element 404 to be S-polarized light and then impinges upon the half-silvered prism 408 after traveling in the horizontal direction as seen in FIG. 2. Whereas, the S-polarized light reflected by the reflection surface of the polarization beam splitter 402 is reflected by the mirrors 405, 406 and 407 and then impinges upon the half-silvered prism 408 after traveling in the perpendicular direction as seen in FIG. 2. In the half-silvered prism 408, the P-polarized light converted to S-polarized light by the rotating polarization element 404 and the S-polarized light by way of the mirror 407 travel the same optical path and then are reflected by a mirror 409 to impinge upon the spectral means 42.

The spectral means 42 comprises, for instance, a diffractive optics and functions as a spectrometer which spectrally divides the incident interference light L4 and emits the spectrally-divided light toward the light detecting means 44. The light detecting means 44 is formed by an element such as a CCD or a photodiode which comprises a plurality of, for instance, one-dimensionally or two-dimensionally arranged photosensors and each of the photosensors detects each wavelength band of the interference light beam L4 spectrally divided as described above.

The light detecting means 44 is connected to the image obtaining means 50 comprising, for instance, a computer system such as a personal computer and the image obtaining means 50 is connected to a display system 60 formed, for instance, by a CRT or a liquid crystal display system. The image obtaining means 50 obtains reflection information in the position of depth by carrying out frequency analysis on the detected interference light beam L4. Then the image obtaining means 50 obtains a tomographic image on the basis of the intensity of the reflected light L3 in the direction of depth of the object S. The tomographic image is displayed by the displaying system 60.

Here, detection of the interference light beam L4 in the interference light detecting means 40 and image generation in the image obtaining means 50 will be described briefly. Note that a detailed description of these points can be found in M. Takeda, "Optical Frequency Scanning Interference Microscopes", Optical Engineering Contact, Vol. 41, No. 7, pp. 426-432, 2003.

When the measuring light beam L1 is projected onto the object S, the reflected light L3 from each depth of the object S and the reference light L2 interfere with each other with various optical path length difference l. When the light intensity of the interference fringe at this time versus each optical path length difference is assumed to be S(l), the light intensity I(k) detected in the interference light detecting means 40 is expressed by the following formula.

$$I(k) = \int_0^\infty S(l)[l + \cos(kl)]dl \tag{1}$$

wherein k represents the wave number and l represents the optical path length difference. Formula (1) may be considered to be given as an interferogram of a light frequency range having a wave number k as a variable. Accordingly, a tomographic image can be generated by obtaining in the image obtaining means 50 reflection information in each position of depth of the object S by carrying out frequency analysis by Fourier-transform on the spectral interference light detected by the interference light detecting means 40 and determining the intensity S(l) of the interference light beam L4.

Operation of the optical tomography system 1 having a structure described above will be described, hereinbelow. When a tomographic image is to be obtained, the optical path length is first adjusted by moving the movable stage 23 in the direction of the arrow A so that the object S is positioned in the measurable area. The light beam L is subsequently emitted from the light source unit 10 and the light beam L is divided into the measuring light beam L1 and the reference light beam L2 by the dividing means 3. The measuring light beam L1 is led by the optical probe 30 into a body cavity and is projected onto the object S. The reflected light beam L3 from the object S and the reference light beam L2 reflected by the reflecting mirror 22 are multiplexed by the multiplexing means 4, and the interference light beam L4 of the reflected light beam L3 and the reference light beam L2 is detected by the interference light detecting means 40. A tomographic image is obtained by carrying out frequency analysis on a signal of the detected interference light beam L4 in the image obtaining means 50. In the optical tomography system 1 where a tomographic image is obtained by measurement of SD-OCT, reflection information in each position of depth is obtained on the basis of the frequency and the intensity of the interference light beam L4 and movement of the reflecting mirror 22 in the direction of arrow A is employed to adjust the position in which a tomographic image is obtained.

By rotating the probe 30 so that the measuring light beam L1 scans the object S in a one-dimensional direction, information on the direction of depth of the object S is obtained in each part along the direction of scan and accordingly tomographic images on the cross-section including the direction of scan can be obtained. Further, by causing the measuring light L1 to scan in a second direction perpendicular to said direction of scan with respect to the object S, tomographic images on the cross-section including the second direction can be obtained.

As described above, in the optical tomography system 1, since the polarization setting means 41 is provided, the light impinging upon the spectral means 42 is S-polarized light irrespective of the state of polarization of the interference light L4 led by the optical fiber FB4 or even if the state of polarization of the interference light L4 led by the optical fiber FB4 changes. Accordingly, even if an element having polarization characteristics such as a diffractive optics is employed as the spectral means 42, the polarization characteristics can be measured without affected by change in the state of polarization of the interference light L4 led by the optical fiber FB4 and the error in the wavelength spectrum of the interference light L4 due to change in the state of polarization of the interference light L4 which has been conventionally generated can be removed, whereby deterioration of the quality of the tomographic image obtained by Fourier transform of the interference light can be prevented.

The arrangement such as of this example, where the light impinging upon the spectral means 42 is solely an S-polarized light, is effective in wavelength band where $\lambda/d>0.8$ shown in FIG. 9 and the fluctuation in the diffractive efficiency is larger in the P-polarized light than the S-polarized light. Whereas, in the wavelength band near $\lambda/d=0.7$ where the fluctuation in the diffractive efficiency is larger in the S-polarized light, it is preferred that the P-polarized light be caused to enter the spectral means 42. This can be easily realized by moving the rotating polarization element 404 to the optical path for the S-polarized light in the arrangement shown in FIG. 2. What kind of light for the state of polarization is to be caused to impinge upon the spectral means 42 need not be limited to this example, but preferably is suitably selected according to the conditions of light to be employed such as the wavelength band thereof.

When though no optical fiber is employed to guide the interference light L4 from the multiplexing means 4 to the interference light detecting means 40, nevertheless parallel light impinges upon the spectral means 42 in the polarization setting means 41, the collimating lens 401 may be abbreviated.

An optical tomography system in accordance with a second embodiment of the present invention will be described with reference to FIG. 5, hereinbelow. Since the optical tomography system in accordance with the second embodiment differs from the first embodiment in that a polarization setting means 241 differs from that 41 shown in FIG. 2 and is the same as the first embodiment in the other structure, only the polarization setting means 241 is shown.

The polarization setting means 241 comprises a polarization-preserving optical fiber coupler 242 to the input of which the optical fiber FB4 is connected, a pair of polarization-preserving optical fibers 243 and 244 which are connected to the output of the polarization-preserving optical fiber coupler 242, an optical fiber coupler 245 to the input of which the optical fibers 243 and 244 are connected, an optical fiber 246 connected to an output of the optical fiber coupler 245, a collimating lens 247 which makes parallel the light radiated from the optical fiber 246 and a mirror 248 which folds the optical path and causes the parallel light to enter the spectral means 42.

The polarization-preserving optical fiber coupler 242 separates incident light into a pair of linearly polarized light bundles which are respectively polarized in directions perpendicular to each other as the polarization beam splitter, and may be, for instance, a PANDA-PBS (polarization-maintaining and absorption-reducing-polarization beam splitter). The optical fiber coupler 245 functions as a multiplexing means and may be, for instance, a 3 dB optical fiber coupler.

The polarization-preserving optical fibers 243 and 244 are a fiber which guides light holding the direction of polarization of the light and may be, for instance, a PANDA (polarization-maintaining and absorption-reducing) fiber or an ellipsoidal core fiber whose core is non-axial-symmetrical. An example where PANDA fibers are employed as the polarization-preserving optical fibers 243 and 244 will be described, here. As shown in FIG. 6 in cross-section, the PANDA fiber is provided with a pair of stressing portions 263a and 263b on opposite sides of the core 262 centrally disposed in a clad 261. The direction parallel to the direction in which the stressing portions 263a and 263b are arranged is referred to as "the slow axis direction" while the direction perpendicular thereto is referred to as "the fast axis direction", and the linearly polarized light impinging thereupon in the corresponding direction is guided with the direction of polarization being held.

Figure 5:
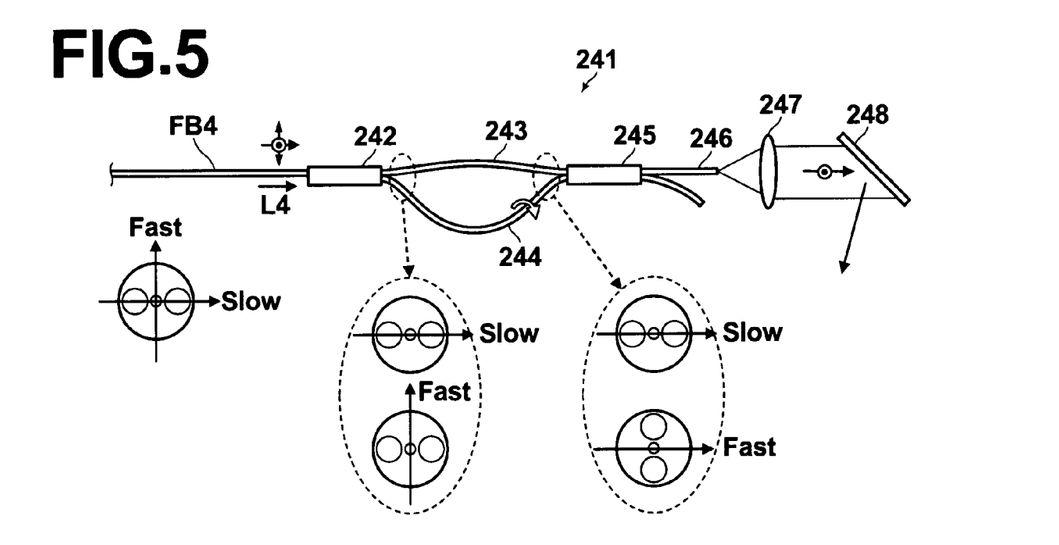
FIG. 5 is a view showing the polarization setting means in an optical tomography system in accordance with a second embodiment of the present invention.
Figure 6:
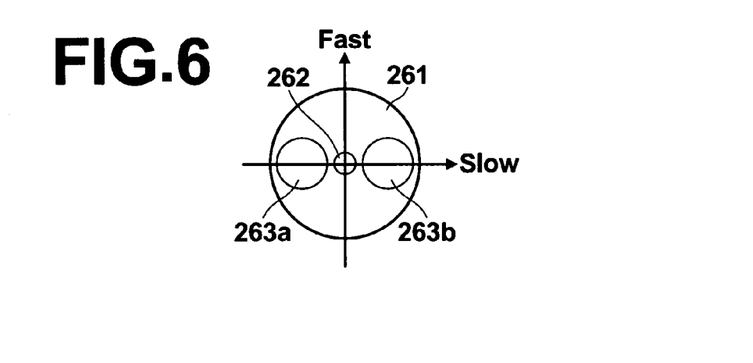
FIG. 6 is a cross-sectional view of the PANDA fiber.

In the polarization setting means 241, instead of inserting the rotating polarization element 404 in the first embodiment, the pair of linearly polarized lights to be synthesized are equalized in their direction of polarization by connecting the polarization-preserving optical fiber 244 to the optical fiber coupler 245 after rotating the polarization-preserving optical fiber 244 by 90° as shown by the white arrow in FIG. 5.

In the polarization setting means 241, instead of providing the optical path length adjusting means 410 in the first embodiment, the polarization-preserving optical fibers 243 and 244 are different in length from each other whereby the lights guided by the two optical fibers do not interfere with each other when they are multiplexed at the optical fiber coupler 245.

The interference light L4 radiated from the optical fiber FB4 is separated into two bundles of light which are respectively polarized in the direction of the slow axis and in the direction of fast axis by the polarization-preserving optical fiber coupler 242 in the polarization setting means 241, and the lights are guided respectively by the polarization-preserving optical fibers 243 and 244. A cross-section of each of the polarization-preserving optical fibers 243 and 244 is shown in an ellipsoidal box in broken line in FIG. 5 and similarly, the direction of polarization of the light guided by each of the polarization-preserving optical fibers 243 and 244 is shown in an ellipsoidal box in broken line in FIG. 5. The light guided by the polarization-preserving optical fiber 244 which is polarized in the direction of fast axis is polarized in the vertical direction immediately after passing through the polarization-preserving optical fiber coupler 242 and is polarized in the horizontal direction or right-and-left direction when impinging upon the optical fiber coupler 245 as shown in FIG. 5 since the polarization-preserving optical fiber 244 is rotated by 90° on the way. Whereas, the light guided by the polarization-preserving optical fiber 243 which is polarized in the direction of slow axis enters the optical fiber coupler 245 with its direction of polarization held unchanged. In the optical fiber coupler 245, these two bundles of light are synthesized into a single linearly polarized light polarized in the right-and-left direction, and the light is reflected by the mirror 28 to impinge upon the spectral means 42 after made parallel by the collimating lens 247 by way of the optical fiber 246.

In the polarization setting means 241 in accordance with the second embodiment described above, effects similar to those in the polarization setting means 41 in accordance with the first embodiment described above can be obtained. Though the polarization-preserving optical fiber 244 is rotated by 90° in this example, the polarization-preserving optical fiber 243 may be rotated by 90°.

Figure 7:
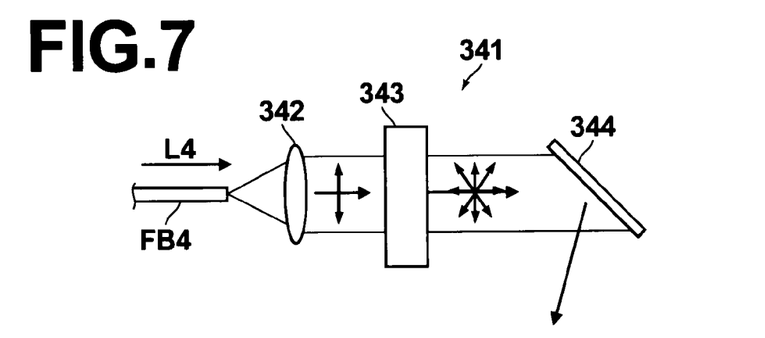
FIG. 7 is a view showing the polarization setting means in an optical tomography system in accordance with a third embodiment of the present invention.

An optical tomography system in accordance with a third embodiment of the present invention will be described with reference to FIG. 5, hereinbelow. Since the optical tomography system in accordance with the third embodiment differs from the first embodiment in that a polarization setting means 341 differs from that 41 shown in FIG. 2 and is the same as the first embodiment in the other structure, only the polarization setting means 341 is shown.

The polarization setting means 341 comprises a collimating lens 342 which makes parallel the interference light L4 from the optical fiber FB4, a polarization releasing element 343 which makes the parallel light non-polarized light and a mirror 344 which folds the optical path.

The polarization releasing element 343 is an optical element which makes all the light non-polarized light, and may comprise a known polarization releasing plate whose detailed structure is disclosed, for instance, in Japanese Patent Publication No. 3(1991)-046802.

In the polarization setting means 341, the interference light L4 radiated from the optical fiber FB4 is made parallel by the collimating lens 342, converted to non-polarized light by the polarization releasing element 343 and then is reflected by the mirror 344 to impinging upon the spectral means 42.

In this embodiment, the light impinging upon the spectral means 42 is non-polarized light irrespective of the state of polarization of the interference light L4 led by the optical fiber FB4 or even if the state of polarization of the interference light L4 led by the optical fiber FB4 changes. Accordingly, even if an element having polarization characteristics such as a diffractive optics is employed as the spectral means 42, the polarization characteristics can be measured without affected by change in the state of polarization of the interference light L4 led by the optical fiber FB4 and the error in the wavelength spectrum of the interference light L4 due to change in the state of polarization of the interference light L4 which has been conventionally generated can be removed, whereby deterioration of the quality of the tomographic image obtained by Fourier transform of the interference light can be prevented.

Figure 8:
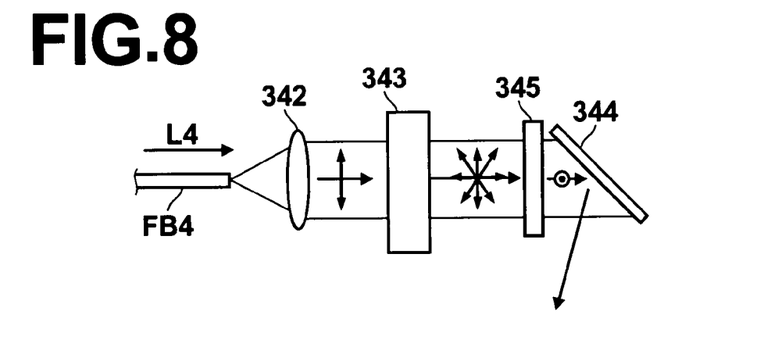
FIG. 8 is a view showing the polarization setting means in the optical tomography system in accordance with a modification of first embodiment of the present invention.

Further, a polarizer 345 which is permeable to only linearly polarized light polarized in a predetermined direction may be disposed between the polarization releasing element 343 and the mirror 344 in the third embodiment as shown in FIG. 8 so that only linearly polarized light polarized in a predetermined direction can impinge upon the spectral means 42. Though in FIG. 8, the case where light passing through the polarizer 345 is polarized in a direction perpendicular to the surface of figure is illustrated by way of example, the linearly polarized light can be polarized in any desired direction by rotating the polarizer 345 about the optical axis. For example, in the case where a component of light polarized in a predetermined direction is not preferable to the spectral means 42, the component of light in the un-preferable direction can be removed by the use of the polarizer 345.

The structure of the polarization setting means need not be limited to those illustrated in conjunction with the above embodiments so long as it can sets the state of polarization of the interference light to a predetermined state irrespective of the state of polarization of the interference light and a predetermined state of polarization of interference light can impinge upon the spectral means.

What is claimed is:

1. An optical tomography system comprising
a light source which emits light,
a light dividing means which divides the light emitted from the light source into measuring light and reference light,
a multiplexing means which multiplexes the reflected light from the object when the measuring light emitted is projected onto the object and the reference light,
an interference light detecting means which has a spectrometer spectrally dividing interference light of the reflected light which has been multiplexed by the multiplexing means and detects the reference light which has been spectrally divided by the spectrometer,
a waveguide means which guides the interference light to the interference light detecting means and
a tomographic image obtaining means which obtains a tomographic image of the object on the basis of the interference light detected by the interference light detecting means,
wherein the improvement comprises that a polarization setting means which causes the interference light guided by the waveguide means to enter the spectrometer after setting the state of polarization of the interference light guided by the waveguide means to a predetermined state of polarization is provided between the waveguide means and the spectrometer.

2. An optical tomography system as defined in claim 1 in which the polarization setting means sets the state of polarization to linearly polarized light.

3. An optical tomography system as defined in claim 2 in which the polarization setting means divides the interference light into two bundles of linearly polarized light which are perpendicular to each other in the direction of polarization and then synthesizes them after changing the direction of polarization of one of them to be the same as the other.

4. An optical tomography system as defined in claim 3 further comprising an optical path length adjusting means which adjusts the optical path length of one of the two bundles of linearly polarized light.

5. An optical tomography system as defined in claim 1 in which the polarization setting means sets the state of polarization to non-polarized light.

* * * * *